United States Patent [19]

Schmitt et al.

[11] Patent Number: 4,521,412

[45] Date of Patent: Jun. 4, 1985

[54] PESTICIDAL IODOPROPARGYLAMMONIUM SALTS

[75] Inventors: Hans-Georg Schmitt; Paul Reinecke, both of Leverkusen; Wilfried Paulus, Krefeld; Hermann Genth, Krefeld; Walter Radt, Krefeld, all of Fed. Rep. of Germany

[73] Assignee: Bayer Aktiengesellschaft, Leverkusen, Fed. Rep. of Germany

[21] Appl. No.: 490,899

[22] Filed: May 2, 1983

[30] Foreign Application Priority Data

May 14, 1982 [DE] Fed. Rep. of Germany ....... 3218176

[51] Int. Cl.$^3$ .................. A01N 43/64; A01N 33/12; C07D 487/12
[52] U.S. Cl. .................................. 514/244; 544/185; 260/439 CY; 564/288; 564/291; 514/502; 514/642
[58] Field of Search ................ 564/288, 291; 544/185; 260/439 R, 439 CY; 424/244, 295, 329; 570/189

[56] References Cited

U.S. PATENT DOCUMENTS

| | | | |
|---|---|---|---|
| 3,135,655 | 6/1964 | Wotiz et al. | 570/189 |
| 3,575,929 | 4/1971 | Jones | 564/291 |
| 4,343,647 | 8/1982 | Dunbar et al. | 564/288 |

FOREIGN PATENT DOCUMENTS

| | | | |
|---|---|---|---|
| 3911365 | 6/1964 | Japan | 564/288 |
| 858719 | 1/1961 | United Kingdom | 564/291 |
| 539867 | 7/1975 | U.S.S.R. | 564/291 |

OTHER PUBLICATIONS

Chemical Abstracts, vol. 73, No. 17, Oct. 26, 1970, p. 32, Haruna et al., "Specific Inhibitor for RNA Replicase".
Kai et al., Chemical Abstracts, 70:11109p, (1969).
Focella et al., Chemical Abstracts, 71:61252w, (1969).
Kai et al., Chemical Abstracts, 72:31696x, (1970).
Kai et al., Chemical Abstracts, 74:99445m, (1971).

Primary Examiner—Natalie Trousof
Assistant Examiner—Bruce D. Gray
Attorney, Agent, or Firm—Sprung, Horn, Kramer & Woods

[57] ABSTRACT

The present invention relates to iodopropargyl-ammonium salts of the formula (I)

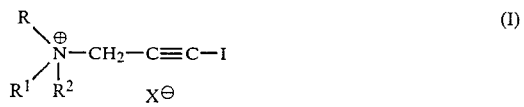

in which
R, $R^1$, $R^2$ and $X^\ominus$ have the meanings given in the description.

They are obtained, for example, by reacting tertiary amines with an iodopropargyl halide. In a second reaction step, the halogen anion can be exchanged for other anions, such as phosphate and sulphate. The iodopropargylammonium salts of the formula (I) are distinguished by high activity as pest-combating agents, in particular by a fungicidal as well as bactericidal activity.

11 Claims, No Drawings

PESTICIDAL IODOPROPARGYLAMMONIUM SALTS

The present invention relates to new iodopropargyl-ammonium salts, processes for their preparation, and their use as pest-combating agents, in particular as fungicides.

It has long been known that N-sulphenylated dicarboxylic acid imides have a fungicidal activity (see German Pat. No. 1,193,498). Furthermore, bis-(halogenoalkinyloxymethyl)-ammonium salts are described as corrosion inhibitors or as microbicides for water treatment (see U.S. Pat. No. 4,206,233). Nothing is stated concerning their use for combating fungal diseases.

New iodopropargylammonium salts of the formula (I)

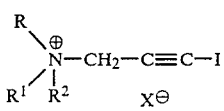

in which
R and $R^1$ are identical or different and represent an aliphatic radical,
$R^2$ represents an aliphatic radical or an aralkyl radical which is optionally monosubstituted or polysubstituted by identical or different substituents, or represents a ferrocenylmethyl radical, or
R, $R^1$ and $R^2$, together with the nitrogen atom, form a ring which can be interrupted by further nitrogen atoms, and
$X^\ominus$ represents an anion.

The iodopropargylammonium salts of the formula (I)

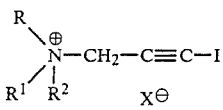

in which
R and $R^1$ are identical or different and represent an aliphatic radical,
$R^2$ represents an aliphatic radical or an aralkyl radical which is optionally monosubstituted or polysubstituted by identical or different substituents, or represents a ferrocenylmethyl radical, or
R, $R^1$ and $R^2$, together with the nitrogen atom, form a ring which can be interrupted by further nitrogen atoms, and
$X^\ominus$ represents an anion,
are obtained by a process in which
(a) tertiary amines of the formula (II)

in which
R, $R^1$ and $R^2$ have the meaning given above, are reacted with an iodopropargyl compound of the formula (III)

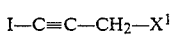

in which
$X^1$ represents halogen or a sulphonate radical, if appropriate in the presence of a diluent, at temperatures between 0° and 110° C., or
(b) tertiary iodopropargylamines of the formula (IV)

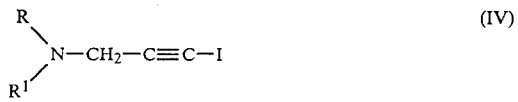

in which
R and $R^1$ have the meanings given above, are reacted with compounds of the formula (V)

$$R^2X^2 \quad (V)$$

in which
$R^2$ has the meaning given above and
$X^2$ represents halogen, alkyl-sulphate or the alkyl-sulphonate or aryl-sulphonate radical,
if appropriate in the presence of a diluent, at temperatures between 0° and 110° C., or
(c) the iodopropargylammonium halides according to the invention, obtained inter alia under (a) or (b) and of the formula (VI)

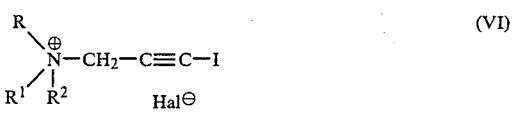

in which
R, $R^1$ and $R^2$ have the meanings given above and
$Hal^\ominus$ represents a halogen anion,
are reacted with compounds of the formula (VII)

in which
Y represents an anionic radical with the preferred meaning of $X^\ominus$, except for halogen, and
B represents an alkali metal cation or alkaline earth metal cation.

The iodopropargylammonium salts according to the invention, of the formula (I), have powerful microbicidal properties. Surprisingly, the compounds according to the invention exhibit, in this respect, a substantially higher action than the N-sulphenylated dicarboxylic acid imides known from the prior art, such as N-trichloromethylthiotetrahydrophthalimide, which is a similar compound in terms of its action.

Among the new iodopropargylammonium salts of the formula (I), those compounds are preferred in which
R and $R^1$ are identical or different and represent a straight-chain or branched alkyl radical,
$R^2$ represents a straight-chain or branched alkyl radical or a benzyl or phenylethyl radical which is optionally monosubstituted to pentasubstituted in the phenyl ring, or represents the ferrocenylmethyl radical, or
R, $R^1$ and $R^2$, together with the nitrogen atom, form a Urotropin radical, and
$X^\ominus$ represents a halogen, phosphate, acetate, benzoate, citrate, tartrate, alkyl- or aryl-sulphonate, alkyl-sulphate, benzisothiazolinone or saccharine anion.

Particularly preferred iodopropargylammonium salts of the formula (I) are those in which R and R¹ are identical or different and represent straight-chain or branched alkyl having 1 to 20 carbon atoms per alkyl radical, R² represents straight-chain or branched alkyl having 4 to 20 carbon atoms, ferrocenylmethyl, benzyl or phenethyl, it being possible in each case for the phenyl ring to be monosubstituted to pentasubstituted by identical or different substituents, amongst alkyl and halogen, or R, R¹ and R², together with the nitrogen atom, form the Urotropin radical, and X⊖ represents a chlorine, phosphate, acetate, benzoate, citrate, tartrate, benzisothiazolinone or saccharin anion, alkyl-sulphonate having 1 to 3 carbon atoms in the alkyl part, preferably methyl-sulphonate and ethyl-sulphonate, aryl-sulphonate wherein the aryl radical can be optionally monosubstituted or disubstituted by alkyl having 1 to 3 carbon atoms, preferably phenyl-sulphonate and toluene-sulphonate, or alkyl-sulphate having 1 to 3 carbon atoms per alkyl radical, in particular the methyl- and ethyl-sulphate radical.

In addition to the compounds of the formula (I) which are mentioned in the preparation examples, the following compounds may also be mentioned individually:

(1-iodopropargyl)-dimethyl-n-butyl-ammonium chloride
(1-iodopropargyl)-diethyl-n-butyl-ammonium chloride
(1-iodopropargyl)-di-n-propyl-n-butyl-ammonium chloride
(1-iodopropargyl)-di-iso-propyl-n-butyl-ammonium chloride
(1-iodopropargyl)-di-iso-butyl-n-butyl-ammonium chloride
(1-iodopropargyl)-di-sec.-butyl-n-butyl-ammonium chloride
(1-iodopropargyl)-di-pentyl-n-butyl-ammonium chloride
(1-iodopropargyl)-di-hexyl-n-butyl-ammonium chloride
(1-iodopropargyl)-dimethyl-heptyl-n-butyl-ammonium chloride
(1-iodopropargyl)-di-octyl-n-butyl-ammonium chloride
(1-iodopropargyl)-di-nonyl-n-butyl-ammonium chloride
(1-iodopropargyl)-di-decyl-n-butyl-ammonium chloride
(1-iodopropargyl)-di-dodecyl-n-butyl-ammonium chloride
(1-iodopropargyl)-di-hexyl-methyl-ammonium chloride
(1-iodopropargyl)-di-pentyl-methyl-ammonium chloride
(1-iodopropargyl)-di-n-butyl-methyl-ammonium chloride
(1-iodopropargyl)-di-sec.-butyl-methyl-ammonium chloride
(1-iodopropargyl)-di-iso-butyl-methyl-ammonium chloride
(1-iodopropargyl)-di-pentyl-methyl-ammonium chloride
(1-iodopropargyl)-di-hexyl-methyl-ammonium chloride
(1-iodopropargyl)-di-heptyl-methyl-ammonium chloride
(1-iodopropargyl)-di-octyl-methyl-ammonium chloride
(1-iodopropargyl)-di-nonyl-methyl-ammonium chloride
(1-iodopropargyl)-di-decyl-methyl-ammonium chloride
(1-iodopropargyl)-di-dodecyl-methyl-ammonium chloride
(1-iodopropargyl)-di-pentyl-ethyl-ammonium chloride
(1-iodopropargyl)-di-hexyl-ethyl-ammonium chloride
(1-iodopropargyl)-di-heptyl-ethyl-ammonium chloride
(1-iodopropargyl)-di-octyl-ethyl-ammonium chloride
(1-iodopropargyl)-di-nonyl-ethyl-ammonium chloride
(1-iodopropargyl)-di-decyl-ethyl-ammonium chloride
(1-iodopropargyl)-di-dodecyl-ethyl-ammonium chloride
(1-iodopropargyl)-di-methyl-benzyl-ammonium chloride
(1-iodopropargyl)-di-ethyl-benzyl-ammonium chloride
(1-iodopropargyl)-di-n-propyl-benzyl-ammonium chloride
(1-iodopropargyl)-di-iso-propyl-benzyl-ammonium chloride
(1-iodopropargyl)-di-n-butyl-benzyl-ammonium chloride
(1-iodopropargyl)-di-iso-butyl-benzyl-ammonium chloride
(1-iodopropargyl)-di-sec.-butyl-benzyl-ammonium chloride
(1-iodopropargyl)-di-pentyl-benzyl-ammonium chloride
(1-iodopropargyl)-di-hexyl-benzyl-ammonium chloride
(1-iodopropargyl)-di-heptyl-benzyl-ammonium chloride
(1-iodopropargyl)-di-octyl-benzyl-ammonium chloride
(1-iodopropargyl)-di-nonyl-benzyl-ammonium chloride
(1-iodopropargyl)-di-decyl-benzyl-ammonium chloride
(1-iodopropargyl)-di-dodecyl-benzyl-ammonium chloride
(1-iodopropargyl)-di-methyl-phenethyl-ammonium chloride
(1-iodopropargyl)-di-ethyl-phenethyl-ammonium chloride
(1-iodopropargyl)-di-n-propyl-phenethyl-ammonium chloride
(1-iodopropargyl)-di-iso-propyl-phenethyl-ammonium chloride
(1-iodopropargyl)-di-n-butyl-phenethyl-ammonium chloride
(1-iodopropargyl)-di-sec.-butyl-phenethyl-ammonium chloride
(1-iodopropargyl)-di-iso-butyl-phenethyl-ammonium chloride
(1-iodopropargyl)-di-pentyl-phenethyl-ammonium chloride
(1-iodopropargy)-di-hexyl-phenethyl-ammonium chloride
(1-iodopropargyl)-di-heptyl-phenethyl-ammonium chloride
(1-iodopropargyl)-di-octyl-phenethyl-ammonium chloride
(1-iodopropargyl)-di-nonyl-phenethyl-ammonium chloride
(1-iodopropargyl)-di-decyl-phenethyl-ammonium chloride
(1-iodopropargyl)-di-dodecyl-phenethyl-ammonium chloride
(1-iodopropargyl)-tri-pentyl-ammonium chloride
(1-iodopropargyl)-tri-heptyl-ammonium chloride
(1-iodopropargyl)-tri-nonyl-ammonium chloride
(1-iodopropargyl)-di-methyl-(2-chlorophenethyl)-ammonium chloride
(1-iodopropargyl)-di-ethyl-(2-chlorophenethyl)-ammonium chloride (1-iodopropargyl)-di-propyl-(2-chlorophenethyl)-ammonium chloride
(1-iodopropargyl)-di-butyl-(2-chlorophenethyl)-ammonium chloride
(1-iodopropargyl)-di-pentyl-(2-chlorophenethyl)-ammonium chloride
(1-iodopropargyl)-di-hexyl-(2-chlorophenethyl)-ammonium chloride
(1-iodopropargyl)-di-heptyl-(2-chlorophenethyl)-ammonium chloride
(1-iodopropargyl)-di-octyl-(2-chlorophenethyl)-ammonium chloride
(1-iodopropargyl)-di-nonyl-(2-chlorophenethyl)-ammonium chloride
(1-iodopropargyl)-di-methyl-(4-chlorophenethyl)-ammonium chloride
(1-iodopropargyl)-di-ethyl-(4-chlorophenethyl)-ammonium chloride
(1-iodopropargyl)-di-propyl-(4-chlorophenethyl)-ammonium chloride
(1-iodopropargyl)-di-butyl-(4-chlorophenethyl)-ammonium chloride
(1-iodopropargyl)-di-pentyl-(4-chlorophenethyl)-ammonium chloride
(1-iodopropargyl)-di-hexyl-(4-chlorophenethyl)-ammonium chloride
(1-iodopropargyl)-di-heptyl-(4-chlorophenethyl)-ammonium chloride
(1-iodopropargyl)-di-octyl-(4-chlorophenethyl)-ammonium chloride
(1-iodopropargyl)-di-nonyl-(4-chlorophenethyl)-ammonium chloride
(1-iodopropargyl)-di-decyl-(4-chlorophenethyl)-ammonium chloride
(1-iodopropargyl)-di-dodecyl-(4-chlorophenethyl)-ammonium chloride
(1-iodopropargyl)-di-methyl-dodecyl-ammonium chloride
(1-iodopropargyl)-di-ethyl-dodecyl-ammonium chloride
(1-iodopropargyl)-di-propyl-dodecyl-ammonium chloride
(1-iodopropargyl)-di-butyl-dodecyl-ammonium chloride
(1-iodopropargyl)-di-pentyl-dodecyl-ammonium chloride
(1-iodopropargyl)-di-hexyl-dodecyl-ammonium chloride
(1-iodopropargyl)-di-heptyl-dodecyl-ammonium chloride
(1-iodopropargyl)-di-octyl-dodecyl-ammonium chloride
(1-iodopropargyl)-di-nonyl-dodecyl-ammonium chloride
(1-iodopropargyl)-di-decyl-dodecyl-ammonium chloride
(1-iodopropargyl)-di-methyl-(2,4-dichlorobenzyl)-ammonium chloride
(1-iodopropargyl)-di-ethyl-(2,4-dichlorobenzyl)-ammonium chloride
(1-iodopropargyl)-di-propyl-(2,4-dichlorobenzyl)-ammonium chloride
(1-iodopropargyl)-di-butyl-(2,4-dichlorobenzyl)-ammonium chloride
(1-iodopropargyl)-di-pentyl-(2,4-dichlorobenzyl)-ammonium chloride
(1-iodopropargyl)-di-hexyl-(2,4-dichlorobenzyl)-ammonium chloride
(1-iodopropargyl)-di-heptyl-(2,4-dichlorobenzyl)-ammonium chloride
(1-iodopropargyl)-dimethyl-(2,4,6-trichlorobenzhyl)-ammonium chloride
(1-iodopropargyl)-di-ethyl-(2,4,6-trichlorobenzyl)-ammonium chloride
(1-iodopropargyl)-di-propyl-(2,4,6-trichlorobenzyl)-ammonium chloride
(1-iodopropargyl)-di-butyl-(2,4,6-trichlorobenzyl)-ammonium chloride
(1-iodopropargyl)-di-pentyl-(2,4,6-trichlorobenzyl)-ammonium chloride
(1-iodopropargyl)-di-hexyl-(2,4,6-trichlorobenzyl)-ammonium chloride
(1-iodopropargyl)-di-heptyl-(2,4,6-trichlorobenzyl)-ammonium chloride
(1-iodopropargyl)-di-octyl-(2,4,6-trichlorobenzyl)-ammonium chloride
(1-iodopropargyl)-di-methyl-(2-methylbenzyl)-ammonium chloride
(1-iodopropargyl)-di-ethyl-(2-methylbenzyl)-ammonium chloride
(1-iodopropargy)-di-propyl-(2-methylbenzyl)-ammonium chloride
(1-iodopropargyl)-di-butyl-(2-methylbenzyl)-ammonium chloride
(1-iodopropargyl)-di-pentyl-(2-methylbenzyl)-ammonium chloride
(1-iodopropargyl)-di-hexyl-(2-methylbenzyl)-ammonium chloride
(1-iodopropargyl)-di-heptyl-(2-methylbenzyl)-ammonium chloride
(1-iodopropargyl)-di-methyl-(2,6-dimethylbenzyl)-ammonium chloride
(1-iodopropargyl)-di-ethyl-(2,6-dimethylbenzyl)-ammonium chloride
(1-iodopropargyl)-di-propyl-(2,6-dimethylbenzyl)-ammonium chloride
(1-iodopropargyl)-di-butyl-(2,6-dimethylbenzyl)-ammonium chloride
(1-iodopropargyl)-di-pentyl-(2,6-dimethylbenzyl)-ammonium chloride
(1-iodopropargyl)-di-hexyl-(2,6-dimethylbenzyl)-ammonium chloride
(1-iodopropargyl)-di-heptyl-(2,6-dimethylbenzyl)-ammonium chloride
(1-iodopropargyl)-di-nonyl-(2,6-dimethylbenzyl)-ammonium chloride and the corresponding alkyl-sulphate, phosphate, acetate, benzoate, citrate, tartrate, benzisothiazolinone and saccharin salts in each case, and also the alkyl- or aryl-sulphonate compounds.

The individual process variants can be represented as follows:

If, for example, tripentylamine and iodopropargyl chloride are used as starting materials in process variant (a), the course of the reaction can be described by the following equation:

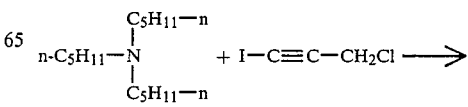

-continued

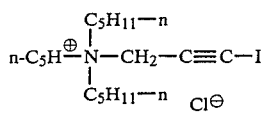

If, for example, dimethyl-3-iodopropargyl-amine and n-butyl chloride are used as starting materials in process variant (b), the course of the reaction can be represented by the following equation:

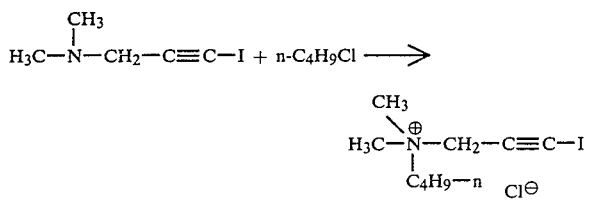

If trihexyl-(1-iodopropargyl)-ammonium chloride and sodium benzoate are used as starting materials in process variant (c), the course of the reaction can be represented by the following equation:

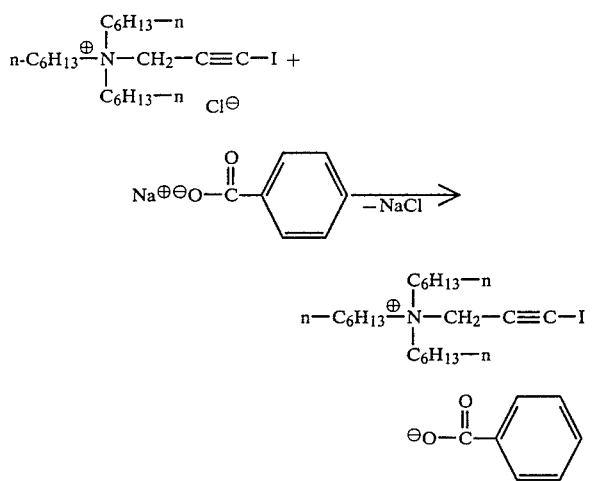

Formula (II) gives a general definition of the tertiary amines employed in the preparation processes described above. Such compounds are known and can be prepared by processes which are in themselves known (see Houben-Weyl, Vol. 11/1, Thieme Verlag, Stuttgart, 1957).

Iodopropargyl compounds of the formula (III) which are furthermore to be used as starting materials are compounds which are known from the literature, and can be prepared by known processes (see, for example, H. G. Viehe: The Chemistry of Acetylenes. Page 689; M. Dekker, New York, 1969).

The tertiary iodopropargylamines to be employed in process variant (b) are represented by formula (IV), and the majority of them are known or can be prepared by processes which are known from the literature, for example by reacting propargyl halides with dialkylamines, followed by iodination (see Japanese Pat. No. 70 41,008). The compounds of the formula (V) which are furthermore to be employed are likewise compounds which are known from the literature.

The iodopropargylammonium halides of the formula (VI) which are to be employed in process variant (c) are new and belong to the concept of the invention. They can be prepared from tertiary amines and an iodopropargyl halide, by known processes.

The compounds of the formula (VII) which are furthermore to be employed as starting compounds have been known for a long time and are commercially available compounds which can be prepared by known processes.

Process variants (a) and (b) are preferably carried out using diluents. Suitable diluents are virtually all organic solvents with a certain polarity. These include in particular halogenated hydrocarbons, such as methylene chloride, ethylene chloride, chloroform, carbon tetrachloride, chlorobenzene and o-dichlorobenzene. Furthermore, ethers, such as diethyl ether and dibutyl ether, glycol dimethyl ether, tetrahydrofuran and dioxane; ketones, such as acetone, methyl ethyl ketone, methyl isopropyl ketone and methyl isobutyl ketone; esters, such as methyl acetate and ethyl acetate; nitriles, such as, for example, acetonitrile and propionitrile; aromatics, such as benzene, toluene and xylene, and also alcohols, such as, for example, methanol, ethanol and n- and iso-propanol. Mixtures of diluents can also be employed. Process variant (a) can also be carried out in water.

In process variants (a) and (b), the reaction temperature is between 0° and 110° C., preferably between 20° and 80° C. process variants (a) and (b) are preferably carried out under atmospheric pressure.

The exchange of the cation in process variant (c) is preferably carried out in an aqueous medium, at temperatures between 20° and 100° C., preferably at 20° to 60° C., and under atmospheric pressure.

In a preferred embodiment of process variant (a) or (b) according to the invention, the compound of the formula (II) or (IV), dissolved in one of the stated diluents, is initially introduced, and the starting compound of the formula (III) or (V) is added. The reaction is slightly exothermic. The compounds according to the invention begin to separate out after a few minutes. However, in most cases stirring is continued overnight, and the precipitated product is filtered off under suction and dried on the next day.

In carrying out process variant (c), the new ammonium halide according to the invention, of the formula (VI), is dissolved in water, and the solution is combined with an aqueous solution of the compounds of the formula (VII). In this case, also, stirring is continued for several hours to complete the reaction, preferably at room temperature. The precipitated product is then filtered off under suction and dried.

The anion exchange by process (c) is also possible directly, that is to say the iodopropargylammonium halides of the formula (VI) do not require intermediate isolation, but can be reacted further, directly in solution, with compounds of the formula (VII).

The active compounds according to the invention exhibit a powerful microbicidal action and can be employed in practice for combating undesired microorganisms. The active compounds are suitable for use as plant protection agents and as microbicidal agents for protecting industrial materials.

For example, fungicidal agents are employed in plant protection in particular for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Thizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

The good activity of the compounds according to the invention, of the formula (I), in plant protection, against Leptosphaeria nodorum in wheat should be particularly singled out. In addition, the action against Erysiphe, Puccinia, Cochliobolus sativus and Pyrenophora teres in cereals, the action against apple scab and Oomycetes, and broad fungicidal action in the agar plate test against rice indications and the bactericidal action of these new compounds should be mentioned.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hyrolysis products; as dispersing agents there are suitable: for example ligninsulphite waste liquors and methylcellulose.

Adhesives such as carboxymethylcellulose and natural and synthetic polymers in the form of powders, granules and latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azole dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.001 to 0.02%, are required at the place of action.

The compounds according to the invention are also suitable for protecting industrial materials, as described above.

Industrial materials within the scope of the present invention are products which themselves do not occur naturally but are manufactured from natural or synthetic starting materials. Within the scope of the present invention, the products to be protected are industrial materials which can be infested and/or decomposed by micro-organisms.

Industrial materials which are to be protected by the substances according to the invention from microbial modification and destruction are, for example, adhesives, glues, papers and cardboards, textiles, leather, wood, coating compositions, plasters, cooling lubricants, sealing compositions and plastic articles, which can be infested or decomposed by microorganisms. Within the scope of the materials to be protected, parts of production plants, such as, for example, cooling water circulations and cooling lubricant circulations, the operational efficiency of which can be adversely affected by microorganisms may also be mentioned. Preferably, the active compounds according to the invention can be used for protecting adhesives, paper, cardboard, coating films, wood and the like.

Micro-organisms which can cause degradation or modification of the industrial materials are, for example, bacteria, fungi, yeasts, algae and slime organisms. Preferably, the substances according to the invention have a powerful and broad action against fungi and bacteria molds as well as wood-destroying and wood-discoloring fungi are embraced by the fungicidal action.

For example, micro-organisms of the following genera may be mentioned: Alternaria, such as Alternaria tenuis, Aspergillus, such as Aspergillus niger, Aureobasidium, such as Aureobasidium pullulans, Chaetomium, such as Chaetomium globosium, Coniophora, such as Coniophora cerebella, Lentinus, such as Lentinus tigrinus, Penicillium, such as Penicillium glaucum, Polyporus, such as Polyporus versicolor, Sclerophoma, such as Sclerophoma pityophila, Trichoderma, such as Trichoderma viride, or Escherichia, such as Escherichia coli or Staphylococcus, such as Staphylococcus aureus.

Depending on their field of use, the substances according to the invention can be converted into the customary formulations, such as solutions, emulsions, suspensions, powders, pastes and granules. These can be prepared in a manner which is in itself known, for example by mixing the active compounds with an extender which consists of a liquid solvent and/or solid carriers, if appropriate with the use of surface-active agents, such as emulsifiers and/or dispersing agents, and, for example, in the case of the use of extenders, organic solvents can, if appropriate, be used as auxiliary solvents.

Organic solvents for the active compounds can be, for example, alcohols, such as lower alcohols, preferably elthanol or isopropanol, or benzyl alcohol, ketones, such as acetone or methyl ethyl ketone, liquid hydrocarbons, such as petrol fractions, or chlorinated hydrocarbons, such as 1,2-dichloroethane.

The microbicidal agents according to the invention contain in general 10 to 100% by weight, preferably 50 to 60% by weight, of the iodopropargylammonium salts as the active compound.

The use concentration of the substances according to the invention depends on the type and occurrence of the micro-organisms to be combated and on the composition of the material to be protected. The optimum use amount can be determined by test series. In general, the use concentrations are in the range from 0.001 to 5% by weight, preferably from 0.01 to 1% by weight, based on the material to be protected.

The new active compounds according to the invention can also be present as a mixture with other known active compounds. The following active compounds may be mentioned as examples: benzimidazolyl carbamates, trihalogenomethylthio compounds, such as N-fluorodichloromethylthio-phthalimide and N,N-dimethyl-N'-phenyl-N'-(fluorodichloromethylthio)-sulphamide, compounds which split off formaldehyde, such as hemiformals, phenol derivatives, such as p-chloro-m-cresol, 2-phenyl-phenol and (2,2'-dihydroxy-5,5'-dichloro)-diphenylmethane, dithiocarbamates, thiazolylbenzimidazole, isothiazolone and benzisothiazolone derivatives, tetrachloroisophthalic acid nitrile, mercaptobenzothiazole and mercaptopyridine.

PREPARATION EXAMPLES

Example 1

(Variant a)

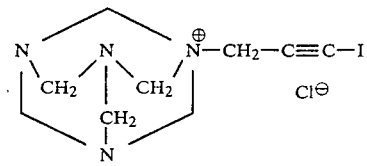

14 g (0.1 mol) of hexamethylenetetramine are dissolved in 800 ml of acetone, and 20 g (0.1 mol) of 3-chloro-1-iodopropyne are added. The reaction is slightly exothermic, and the quarternary salt starts to separate out after about 15 minutes. The mixture is stirred overnight at room temperature, and the pale beige product is then filtered off under suction and dried. 28.2 g (84.7% of theory) of 1-N-(3-iodopropargyl)-hexamethylenetetrammonium chloride of melting point 193°–195° C. are obtained. The compounds of the formula (I)

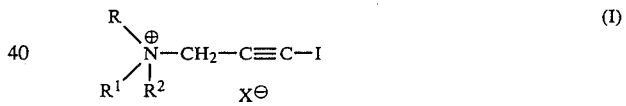

can be obtained analogously:

| Example No. | R | $R^1$ | $R^2$ | $X^\ominus$ | Melting point (°C.) |
|---|---|---|---|---|---|
| 2 | n-$C_4H_9$— | n-$C_4H_9$— | n-$C_4H_9$— | Cl | 167–169 |
| 3 | $C_6H_5$—$CH_2$— | $CH_3$ | $CH_3$ | Cl | 160–162 |
| 4 | n-$C_8H_{17}$— | n-$C_8H_{17}$— | n-$C_8H_{17}$— | Cl | Wax |
| 5 | n-$C_6H_{13}$— | n-$C_6H_{13}$— | n-$C_6H_{13}$— | Cl | Resin |
| 6 | mixture { n-$C_{12}H_{25}$— / n-$C_{14}H_{29}$— } | { $CH_3$ / $CH_3$ } | { $CH_3$ / $CH_3$ } | Cl | 168–170 |
| 7 | ferrocenyl-$CH_2$— | $CH_3$ | $CH_3$ | Cl | >300 |

EXAMPLE 8

(Variant c)

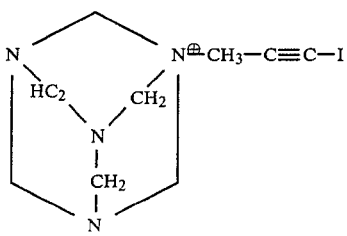 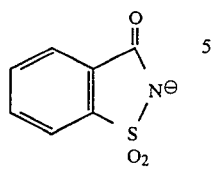 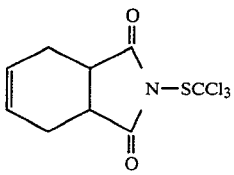

7.1 g (0.029 mol) of sodium saccharin dihydrate are dissolved in 60 ml of water, and 10 g (0.029 mol) of 1-N-(3-iodopropargyl)-hexamethylenetetrammonium chloride are dissolved in 330 ml of water. The two solutions are combined, and stirred at room temperature. The product starts to separate out after about 30 minutes. Stirring is continued overnight at room temperature, and the product is then filtered off under suction and dried in a desiccator. 8.2 g (54% of theory) of 1-N-(3-iodopropargyl)-hexamethylenetetrammonium saccharinate are obtained as a white powder of melting point 189° C.

EXAMPLE 9

As in Example 8, 1-N-(3-idodopropargyl)-hexamethylenetetrammonium (benzisothiazolin-3-on)-ate

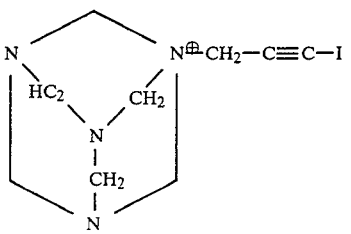 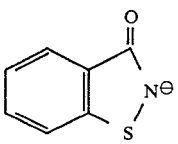

can be obtained in a yield of 48%, as a pale brown product of melting point 103°–105° C.

EXAMPLE 10

Example 10 can be prepared as described in Example 8. The compound

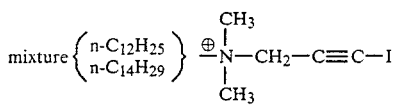

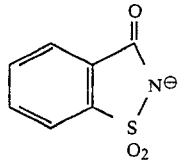

is obtained as a white powder of melting point 97°–100° C.

Use Examples

In Use Example A which follows, the comparative substance indicated below was employed:

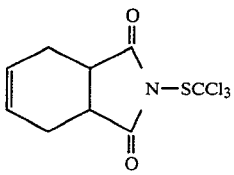

Example A

Leptosphaeria nodorum test (wheat)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the compound known from the prior art is shown, for example, by the compounds according to the following preparation examples: 5, 4, 8 and 10.

EXAMPLE B

Action against fungi

The compounds according to the invention were incorporated, in stepwise concentrations between 20 and 5,000 mg/l of test sample, into an agar prepared from beerwort and peptone. After the agar had solidified, the agar samples thus prepared were contaminated with pure cultures of various test fungi, such as Aspergillus niger, Chaetomium globosum and Penicillium glaucum.

After storage for two weeks at 28° C. and 60 to 70% relative atmospheric humidity, the evaluation was carried out. The smallest concentration of the substance contained in an agar sample at which no growth of the species used took place is given as the minimum inhibitory concentration (MIC).

In this test, compounds according to preparation examples 6, 10, 4, 1, 7 and 3 show a very good action.

EXAMPLE C

Action against bacteria

The active compounds according to the invention are added, in concentrations of 20 to 5,000 ppm, to an agar which contains broth as the nutrient medium. Thereafter, the nutrient medium is infected in each case with Escherichia coli or Staphylococcus aureus, and the infected medium is kept for 2 weeks at 28° C. and 60 to 70% relative atmospheric humidity. The MIC is the lowest concentration of active compound at which no growth of the microbe species used takes place.

In this test, for example, the compounds according to preparation examples 6, 10, 4, 1, 7 and 3 give good results.

EXAMPLE D

Action against slime organisms

The compounds, in concentrations in each case of 0.1 to 100 mg/l in Allen's nutrient solution (Arch. Mikrobiol. 17, 34 to 53 (1952), which contains, in 4 l of sterile water, 0.2 g of ammonium chloride, 4.0 g of sodium nitrate, 1.0 of dipotassium hydrogen phosphate, 0.2 g of calcium chloride, 2.05 g of magnesium sulphate, 0.02 g of iron chloride and 1% of caprolactam, are used dissolved in a small amount of acetone. Shortly beforehand, the nutrient solution is infected with slime organisms (approx. 10$^6$ germs/ml) which were isolated from spinning water circulations used in polyamide production. Nutrient solutions which have the minimum inhibitory concentration (MIC) or greater active compound concentrations are still completely clear after culture for 3 weeks at room temperature, that is to say the pronounced multiplication of the microbes, and slime formation, which are noticeable, after 3 to 4 days, in the nutrient solutions free of active compound are suppressed.

In this test, the compounds according to preparation examples 6, 10, 4, 1, 7 and 3 show good actions.

It will be appreciated that the instant specification and examples are set forth by way of illustration and not limitation, and that various modifications and changes may be made without departing from the spirit and scope of the present invention.

What is claimed is:

1. An iodopropargylammonium salt of the formula

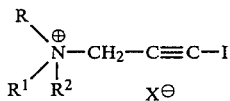

in which
R and R$^1$ each independently is alkyl having 1 to 20 carbon atoms,
R$^2$ is alkyl having 4 to 20 carbon atoms, benzyl, phenethyl, or benzyl or phenethyl which is alkyl and halogen substituted, or a ferrocenylmethyl radical, or
R, R$^1$ and R$^2$, together with the nitrogen atom, form the Urotropin radical, and
X$^\ominus$ is an anion.

2. An iodopropargylammonium salt according to claim 1,
in which
X$^\ominus$ is a halogen, phosphate, acetate, benzoate, citrate, tartrate, sulphonate, sulphate, benzisothiazolinone or saccharin anion.

3. An iodpropargylammonium salt according to claim 1,
in which
X$^\ominus$ is a chlorine, phosphate, acetate, benzoate, citrate, tartrate, benzisothiazolinone or saccharin anion, alkyl-sulphonate radical having 1 to 3 carbon atoms in the alkyl part, a phenyl sulphonate radical which is optionally monosubstituted or disubstituted by alkyl having 1 to 3 carbon atoms, or an alkylsulphate radical having 1 to 3 carbon atoms in the alkyl radical.

4. An iodopropargylammonium salt according to claim 1, wherein such salt is a 1-N-(3-idopropargyl)-tri-n-octyl-ammonium salt of the formula

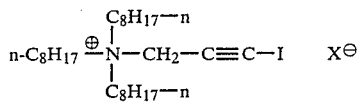

5. An iodoparpargylammonium salt according to claim 1, wherein such salt is a 1-N-(3-idopropargyl)-tri-n-hexyl-ammonium salt of the formula

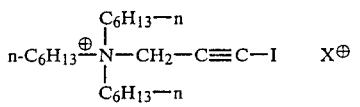

6. An iodpropargylammonium salt according to claim 1, wherein such salt is 1-N-(3-iodopropargyl)-hexamethyl-enetetrammonium saccharinate of the formula

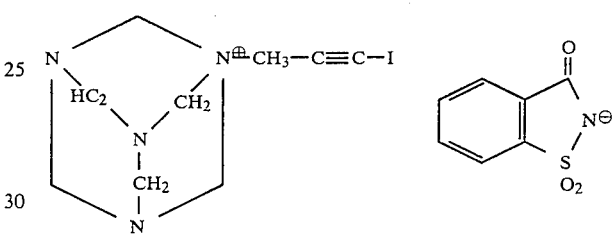

7. An iodopropargylammonium salt according to claim 1, wherein such salt is a mixture of 1-N-(3-idopropargyl)-dimethyl-n-dodecyl- and n-tetradecyl-ammonium saccharinate of the formula

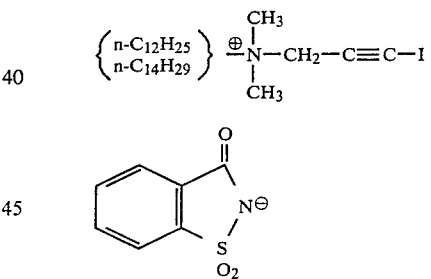

8. A pesticidal composition comprising a pesticidally effective amount of an iodopropargylammonium salt according to claim 1 in admixture with a diluent.

9. A method of combating pests which comprises applying to the pests or to a pest habitat a pesticidally effective amount of an iodopropargylammonium salt according to claim 1.

10. The method according to claim 9, wherein such salt is
a 1-N-(3-iodopropargyl)-tri-n-octyl-ammonium salt,
a 1-N-(3-iodopropargyl)-tri-n-hexyl-ammonium salt,
1-N-(3-iodopropargyl)-hexamethylenetetrammonium saccharinate or
a mixture of 1-N-(3-iodopropargyl)-dimethyl-n-dodecyl- and n-tetradecyl-ammonium saccharinate.

11. An iodopropargylammonium salt according to claim 1, in which
R$^2$ is alkyl having 4 to 20 carbon atoms, benzyl phenethyl, or benzyl or phenylethyl which is alkyl and halogen substituted.

* * * * *

UNITED STATES PATENT AND TRADEMARK OFFICE
CERTIFICATE OF CORRECTION

PATENT NO. : 4,521,412

DATED : June 4, 1985

INVENTOR(S) : Hans-Georg Schmitt, et al

It is certified that error appears in the above-identified patent and that said Letters Patent is hereby corrected as shown below:

| | |
|---|---|
| Col. 6, line 3 | Correct spelling of "trichlorobenzyl" |
| Col. 8, line 29 | Delete "process" and substitute --Process-- |
| Col. 9, line 16 | Delete "and" before "broad" and substitute --the-- |
| Col. 10, line 34 | Before "can" insert --forms-- |
| Col. 11, line 12 | Correct spelling of "globosum" |
| Col. 13, line 1 and Col. 16, line 25 | Delete middle of structure and substitute -- $-CH_2-$ -- |
| Col. 13, line 28, Col. 16, line 2, Col. 16, line 11 and Col. 16, line 34, 35 | Correct spelling of "iodopropargyl" |
| Col. 16, line 10 and Col. 16, line 19 | Correct spelling of "iodopropargylammonium" |
| Col. 16, line 15 | Delete "X ⊕" and substitute --X ⊖ -- |

Signed and Sealed this

Fifteenth Day of October 1985

[SEAL]

Attest:

DONALD J. QUIGG

Attesting Officer

Commissioner of Patents and Trademarks—Designate